United States Patent [19]

Babson et al.

[11] Patent Number: 5,318,748
[45] Date of Patent: Jun. 7, 1994

[54] CENTRIFUGE VESSEL FOR AUTOMATED SOLID-PHASE IMMUNOASSAY HAVING INTEGRAL COAXIAL WASTE CHAMBER

[75] Inventors: Arthur L. Babson, Chester; John E. Underwood, Ramsey, both of N.J.

[73] Assignee: Cirrus Diagnostics, Inc., Randolph, N.J.

[21] Appl. No.: 681,943

[22] Filed: Apr. 8, 1991

Related U.S. Application Data

[60] Division of Ser. No. 552,063, Jul. 13, 1990, Pat. No. 5,084,240, which is a continuation-in-part of Ser. No. 233,337, Jul. 25, 1988, abandoned.

[51] Int. Cl.⁵ .................... G01N 33/544; L12M 1/16
[52] U.S. Cl. ........................................ 422/72; 422/69; 422/102; 436/524; 494/43; 494/44
[58] Field of Search ............... 422/69, 72, 102; 494/43, 44; 436/524

[56] References Cited

U.S. PATENT DOCUMENTS

| | | | |
|---|---|---|---|
| 3,722,790 | 3/1973 | Natelson | 422/101 X |
| 3,841,838 | 10/1974 | Natelson | 422/102 |
| 3,899,296 | 8/1975 | Mailen et al. | 422/72 X |
| 3,953,172 | 4/1976 | Shapiro et al. | 422/72 X |
| 4,111,355 | 9/1978 | Ishimaru | 494/44 X |
| 4,177,921 | 12/1979 | Nielson | 494/44 X |
| 4,314,968 | 2/1982 | Guigan | 422/72 X |
| 4,458,812 | 7/1984 | Dreier et al. | 494/44 X |
| 4,478,946 | 10/1984 | Van der Merwe et al. | 436/518 |
| 4,639,242 | 1/1987 | Babson | 494/37 |
| 4,673,653 | 6/1987 | Guigan | 422/64 X |
| 4,758,409 | 7/1988 | Uffenheimer | 422/102 |
| 4,939,096 | 7/1990 | Tonelli | 435/5 |

Primary Examiner—James C. Housel
Assistant Examiner—A. Soderquist
Attorney, Agent, or Firm—Whitham & Marhoefer

[57] ABSTRACT

A centrifuge vessel (10) for performing automated immunoassays is disclosed. The centrifuge vessel (10) comprises a center tube (11) and an outer waste chamber (15). A biomaterial (18) is held within the center tube (11) and is capable of binding specific analytes in test samples. In operation, the centrifuge vessel (10) is rotated at high speed about its longitudinal axis, thereby causing all fluid within the center tube (11) to be transported into the outer waste chamber (15) while the analyte of interest remains bound to the biomaterial (18) positioned within the center tube (11).

18 Claims, 1 Drawing Sheet

CENTRIFUGE VESSEL FOR AUTOMATED SOLID-PHASE IMMUNOASSAY HAVING INTEGRAL COAXIAL WASTE CHAMBER

CROSS-REFERENCE TO RELATED APPLICATIONS

This patent application is a division application of the co-pending U.S. patent application having the Ser. No. 07/552,063 filed on Jul. 13, 1990, now U.S. Pat. No. 5,084,240, which in turn was a continuation-in-part (CIP) application of the U.S. patent application having Ser. No. 07/233,337 filed on Jul. 25, 1988, now abandoned.

BACKGROUND OF THE INVENTION

1. Field of the Invention

The subject invention is generally related to a centrifuge vessel which is rotated at high speed about its longitudinal axis and, more particularly, to a centrifuge vessel which can be used to separate an analyte from a biological solution in an automated fashion.

2. Description of the Prior Art

Centrifuges are well known commercial and laboratory tools that are used to separate materials of varying densities. Centrifuges are often used for clarifying liquids whereby suspended solids such as cells or proteins are sedimented from solution by high speed rotation of the centrifuge vessel. Two common types of centrifuges are the horizontal centrifuge and the fixed angle centrifuge.

In the conventional horizontal centrifuge, sample containers of the solution to be centrifuged are placed in holders called "buckets". These buckets are subsequently attached to a vertical rotor in a balanced arrangement and swung to a horizontal plane under centrifugal force. While being rotated at high speeds in the horizontal position, the denser particles in the sample move along an unimpeded path toward the bottom of the buckets to form a smooth, even "pellet" of sedimented material. The non-pelleted supernatant solution can be decanted from the bucket once centrifugation is halted.

In the conventional fixed angle centrifuge, a rotor holds a plurality of sample containers at fixed angles relative to the axis of rotation. In the same fashion as in the horizontal centrifuge, at least a pair of sample containers must be used in order to balance the rotor during high speed spinning. During high speed rotation of the fixed angle rotor, the denser particles in the sample containers pellet along the side wall of the container. Pelleting on the side wall does make decanting of the supernatant more difficult because of the possible resuspension of the pellet; however, there are certain advantages in using the fixed angle centrifuge. For example, in the fixed angle centrifuge there is a shorter path for sedimentation resulting in a shorter time for separation and, more importantly, higher speeds of rotation are achievable with fixed angle rotors because they are subjected to less air turbulence than the hanging bucket centrifuges. Higher rotation speeds allow greater centrifugal forces to act on the suspended solids.

As pointed out above, in both the horizontal and the fixed angle centrifuges, the rotor must be balanced accurately in order to prevent damage to the centrifuge. In order to properly balance the rotor, the lab technician must precisely weigh each centrifuge sample container using a balance and then position two sample containers of equal weight in the rotor on opposite sides. This balancing step is very tedious and often requires withdrawing and adding back sample to the sample container until it reaches the desired weight.

In U.S. Pat. No. 4,639,242 to Babson, the complete disclosure of which is incorporated herein by reference, a vessel was described which allowed for the complete physical separation of a precipitate and supernatant in a single tube. In operation, a precipitating agent is first mixed with the biological specimen and given time to react with analyte therein. Then the tube is rotated about its longitudinal axis at high speed. During high speed rotation, the contents of the tube is forced against the inner wall of the tube and moves upward towards the top of the tube due to the tube's inclined inner surface. At the top of the tube, the precipitate is deposited within V-shaped grooves on the tube's interior. After rotation is stopped, the precipitate is retained in the V-shaped grooves at the top of the tube while the liquid drops back to the bottom of the tube.

U.S. Pat. No. 4,639,242 to Babson also discloses a procedure for using the tube whereby a radioactively labelled antibody is bound in the bottom of the tube. The radioactively labelled antibody reacts with an analyte of interest in the biological fluid during a short incubation time during which the biological fluid is permitted to mingle with the bound antibody so that it may bind the analyte of interest. Then the tube is rotated at high speed, thereby causing the fluid in the tube to rise to the top while the analyte remains bound to the antibody in the bottom of the tube. The radioactivity in the bottom of the tube is counted while the tube is spinning.

While the tube disclosed in U.S. Pat. No. 4,639,242 to Babson is more adaptable to an automated processing environment than conventional horizontal and fixed angle centrifuges because it does not require the batch step of balancing pairs of rotor tubes, the Babson tube is not suitable for some of today's processing environments. For example, in some environments it may not be desirable to have a precipitation step. Not only does precipitation require extra chemicals to be used and time for the precipitation reaction to take place, but in some environments precipitation may reduce yield or the precipitating agent itself may affect the measured results. In addition, it may be desirable to stop the tube from spinning and use other instrumentation to make radioactive, fluorescent, or other related readings.

SUMMARY OF THE INVENTION

It is therefore an object of the present invention to provide a centrifuge tube which includes a means for collecting biological fluid and wash liquid during rotation about its longitudinal axis and for storing that biological fluid and wash liquid separate from a bound analyte after the rotation of the centrifuge tube has ceased.

It is another object of this invention to provide a centrifuge tube which includes a waste chamber about its periphery, a cap over its top portion which allows fluid communication between the centrifuge tube and the waste chamber, and a biological material positioned within the centrifuge tube and being restricted from the waste chamber which is capable of binding an analyte of interest present in a biological sample.

According to the invention, a centrifuge tube as been developed which is suitable for performing automated solid phase immunoassays. As a general rule, immunoassays in the clinical laboratory have rapidly replaced other methods used to detect or quantitate substances in body fluids with important biologic or pharmacologic properties. The high levels of sensitivity and specificity achieved with immunoassays result from the specific, high-affinity reversible binding of antigens to antibodies, and from the development of methods for attaching readily detected labels (radioactive isotopes, fluorescent or chemiluminescent molecules, enzymes and the like) to antigens or antibodies. Although radioactive isotopes have been the most extensively used label, they are not preferred because of concerns with radioactivity. Because of these concerns, the number of sensitive, specific immunoassays employing non-radioactive labels is rapidly expanding.

As is generally known among clinicians, many immunoassay procedures are based upon the reaction of an antigen, which is the analyte to be ultimately measured, with an antibody which has been adsorbed or otherwise bound to a solid surface. These solid surfaces (hence the designation "solid-phase immunoassays") may be the interior of small test tubes (such as those available from Micromedic Systems, Inc. of Horsham, Pa.), microtiter trays (such as the 96 well trays available from Amersham International of Bucks, England), macrobeads (such as those available from Abbott Laboratories of Abbott Park, Ill.), or microparticles (such as those available from Pandex Laboratories, Inc. of Mundolein, Ill.), or magnetic particles (such as those available from Corning Medical of Medfield, Mass.). An advantage of solid-phase immunoassay over liquid-phase immunoassay is that common reagents and serum constituents which can potentially interfere with the measurement of the label are removed in the washing step of the procedure. While a variety of immunoassay schemes involving a solid-phase reactant are possible, most schemes utilize a solid-phase antibody and are generally classified as competitive or noncompetitive.

In competitive immunoassays, which are generally used for small molecular weight analytes with only a single antibody binding site, antigen present in the sample or standard competes with a measured amount of labeled antigen for a limited number of binding sites on a solid-phase bound antibody. After removal of any unreacted antigen from the test system, and washing of the solid support material, the bound label is quantitated by suitable means well known in the art. The amount of labeled antigen bound to the solid-phase antibody is inversely related to the concentration of antigen (analyte) in the sample or standard.

In noncompetitive immunoassays, an excess of labeled antibody binds to essentially all of the analyte present in the sample, and an excess of the solid-phase antibody also binds to additional sites on the analyte. These two separate antigen-antibody reactions can be conducted either sequentially, by providing an intermediate washing step if the first reaction is with solid-phase antibody, or simultaneously. After the immunological reactions are allowed to reach equilibrium, the excess labeled antibody is removed, the solid phase is washed and the bound label quantitated by suitable means well known in the art. This type of immunoassay is also called a "sandwich assay" because the antigen is sandwiched between the solid-phase and labeled antibodies. It is also called "immunometric assay" because the amount of label bound is usually a direct and linear function of the antigen concentration within the sample. It is also called "two-site immunoassay" if the labeled and solid-phase antibodies are directed to distinct antigenic determinants on the analyte. This type of assay can only be used with large molecular weight analytes with multiple antibody binding sites.

In an alternative sandwich assay format, the second antibody is unlabeled and the procedure is expanded to include an incubation of the sample with an excess of labeled third antibody specific for the IgG of the animal species from which the second antibody is elicited. In this instance, the immobilized and second antibodies are obtained from different animal species, in order to prevent the binding of labeled third antibody directly to the immobilized antibody. An advantage of this approach is that a single labeled antibody can serve as a common reagent for a number of analytes.

Common to all solid-phase immunoassays is the requirement that all unbound labeled antigen or antibody must be removed by thorough washing of the solid-phase prior to measurement of the label. Washing is a cumbersome procedure, particularly for automated analytical systems. For example, washing coated tubes or microwells by alternately adding and aspirating water or wash solution, as is customarily done, is inefficient since there is always some residual solution in the tube or well after each wash cycle. As many as four to six washes of about 4 ml are required to adequately wash the coated tubes conventionally used in present day immunoassay procedures. Furthermore, provisions must be made to collect all the used wash solutions because they could possibly contain infectious agents from the sample specimens.

The centrifuge vessel according to the present invention offers a number of advantages over the present protocols and apparatus conventionally used in solid-phase immunoassay procedures. The centrifuge vessel includes a central tube member and a peripheral waste chamber. In operation, the analyte being tested for reacts with and is bound to a solid support positioned in the central tube and the excess sample fluid, reagents, and wash fluid are separated from the bound analyte by rotating the tube rapidly about its longitudinal axis. High speed rotation causes the fluids to move up the inclined wall of the central tube and drop into the peripheral waste chamber. Rotation continues until no fluid residue remains in the bottom of the tube. After rotation of the tube is halted, the excess sample fluid, reagents and wash fluid are safely stored in the waste chamber and do not re-mix with the bound analyte in the central tube.

A particular advantage of the present design is that multiple washings of the bound analyte can be performed in a sequential fashion as rapidly as the wash solution can be pipetted into the central tube of the vessel. The ability to wash the bound analyte in the rapid fashion results from the excess fluids being transferred to the waste chamber almost instantaneously because of the high speed centrifugal forces acting on the centrifuge vessel. Because of the speed with which washing is accomplished, multiple vessels may be processed sequentially without impairing sample throughput. The speed of processing the vessels allows for the precise control of the incubation times required by immunoassays, and allows for the normally labor-intensive immunoassay procedure to be automated.

BRIEF DESCRIPTION OF THE DRAWINGS

The various aspects, advantages, and principles of the present invention, and the preferred embodiments thereof, will be best understood by reference to the accompanying drawings in which.

DETAILED DESCRIPTION OF THE PREFERRED EMBODIMENT OF THE INVENTION

Figure 1:
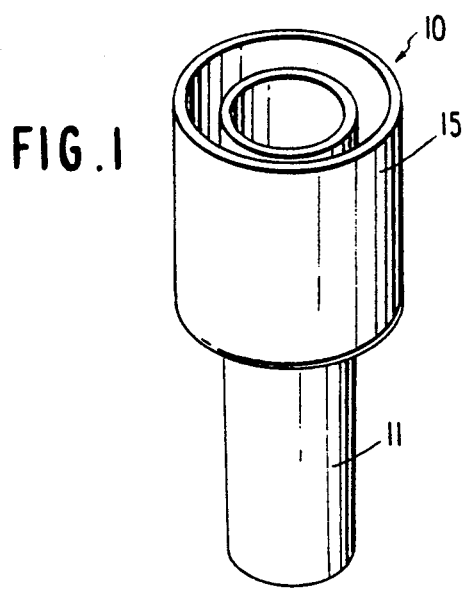
FIG. 1 is a perspective view of a centrifuge vessel.
Figure 2:
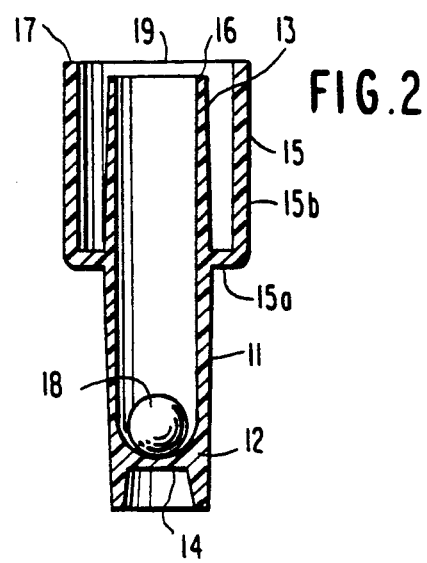
FIG. 2 is a cross-sectional side view of the centrifuge vessel.

Referring now to the drawings and, more particularly to FIGS. 1 and 2, which show the centrifuge vessel 10 comprises a longitudinally extending central tube 11 opened at the top 16 of its upper end portion 13, and sealed at its lower end portion 12. Integrally attached to tube 11 at a point between the upper and lower ends is a generally cylindrical waste chamber 15 having a circumferentially extending bottom portion 15a extending between tube 11 and the waste chamber's upwardly extending cylindrical side wall 15b. The waste chamber 15 is open at its uppermost end 17 at a point above the top 16 of the tube 11. The waste chamber is coaxial with the tube 11, and has an inner diameter greater than the outer diameter of the tube 11.

Although the centrifuge vessel 10 may be manufactured from various materials, for ease of manufacture it is preferred that the vessel be molded from a plastic (polymeric) material which is compatible with its intended use. The uppermost end 17 of waste chamber 15 may be sealed with a metal foil or polymeric membrane 19 to contain the liquid in the vessel as it is spun on its longitudinal axis or, it may, as will be discussed in conjunction with FIGS. 3-6, have a cap welded thereto. If a foil membrane 19 is used, the center of the membrane 19 is punctured to allow addition of the sample and reagents to tube 11. If a welded cap is used, a small foil cover over the central tube 11 is removed to allow the addition of the sample and the reagents.

The lower end 12 of the vessel 10 may be formed with a drive engagement means 14 that would allow a rotating axle member (not shown) to engage and spin the vessel 10 about its longitudinal axis. As depicted in FIG. 2 (although the depiction is for illustration purposes only and the actual engagement means may take other forms), a female socket 14 is adapted to fit in frictional engagement about a male rotor axle (not shown) to provide a union with the spinning rotor axle and thereby provide for the spinning of the vessel about its longitudinal axis. It is also possible to spin the centrifuge vessel 10 about its longitudinal axis using a set of three opposing rollers (not shown) which will engage the side wall of central tube 11 or the side wall 15b of waste chamber 15. If the three roller arrangement were used, the centrifuge vessel 10 would simply be placed between the rollers and at least one of the rollers would be driven at high speed.

As the vessel is spun about its axis, any fluid within the central tube 11 will travel upward along the inner surface of the tube 11. The inner surface of the tube 11 is preferably manufactured in such a manner so that the closed bottom 12 of the tube 11 has a slightly smaller inner diameter than the open top 16. The outward flaring of the inner surface of the tube 11 provides an incline which aids in transporting fluid upward which is driven thereagainst under the centrifugal force. As can be seen in the FIG. 2, the uppermost terminal end 16 of tube 11 is short of the cross-sectional plane passing through and defining the open uppermost end 17 of the chamber 15. This height differential provides a passage which allows fluid to pass from tube 11 into waste chamber 15. Waste chamber 15 may also be manufactured with its inner diameter at the bottom portion 15a being slightly greater than its inner diameter at its uppermost end 17, thereby functioning to hold fluid at a position towards the base of waste chamber 15 as the centrifuge vessel 10 is being spun about its longitudinal axis. The centrifuge vessel 10 does not need to be removed from the drive means to discard biological or wash fluid between washings since all of the wash fluid is transported to and held in waste chamber 15. Therefore, multiple washings are performed simply by repetitively pipetting wash fluid into the vessel 10 and discarding the waste wash fluid by rotating the centrifuge vessel 10 about its longitudinal axis at high speed.

When the centrifuge vessel 10 is being used in immunoassay procedures, the bottom inner portion of the tube 11 may be coated with an antigen or antibody protein (not shown) which binds to the inner surface of the tube 11. This coating preferably extends from the very bottom of the closed end 12 of the tube 11 upwards to a point anywhere less than about 25% of the overall length of tube 11 where the actual length of the coating is a matter of design of the coating process for manufacture of the coated tube. As an alternative to coating the inner surface of the tube 11 with a specific antigen or antibody, or as a means for providing for additional reaction surfaces for the desired immunoassay procedure, a solid support 18 can be placed within the tube 11 where the solid support includes a binding surface, such as a bound antigen or antibody molecule, for selectively binding a specific analyte in the biological fluid under test. Suitable solid supports 18 may include antigen or antibody coated spheres of organic polymers or inorganic polymers. Silica gels are a typical example of inorganic polymers used as binding spheres. Suitable solid supports 18 are commercially available or can be easily manufactured and the choice of support 18 is dependent upon the binding characteristics of the appropriate antigen or antibody or the ligand used to bind the antigen or antibody to the support 18.

As shown in FIG. 2, a metal foil or polymeric membrane seal 19 can be placed over the open end 17 of the vessel 10 to contain the liquid in vessel 10 as it is rotated about its longitudinal axis. It is envisioned that the vessel 10 may be pre-packaged for use in a specific immunoassay test, and in such an instance the vessel 10 will be sealed at the time of manufacture with the interior surface of the central tube pre-coated with the appropriate antigen or antibody or, alternatively, with a coated solid support 18 placed within the central tube 11. In such a pre-packaged format, the vessel will function as a single-use immunoassay reaction vessel. Prior to use, the center of the membrane 19 is punctured to allow the fluid specimen, which might be urine, blood serum or plasma, or other body fluids or body tissue extracts, along with the proper labeled reagent to be added to tube 11.

Figure 6:
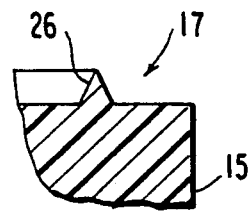
FIG. 6 is an enlarged cross-sectional side view of the bead of material shown in FIG. 5.

As illustrated in FIGS. 3-6, the vessel 10 may be assembled with a hard cover cap 20 instead of a polymer or foil film 19 covering the open end 17 of waste chamber 15. The cap 20 has an outer flange 22 which fits inside and adjacent the inner diameter of sidewall 15b of waste chamber 15 and an outer welding region 24 which is welded to the top 17 of waste chamber 15. As shown in FIG. 6, the top 17 of waste chamber 15 is formed with a bead 26 of extra material which is provided to make the weld with the cap 20 at outer welding region 24. Welding can be accomplished using traditional heat staking or ultra-sonic technologies. It is anticipated that other suitable techniques, such as gluing, could be used for applying the cap 20 to the top 17 of waste chamber 15.

Figure 3:
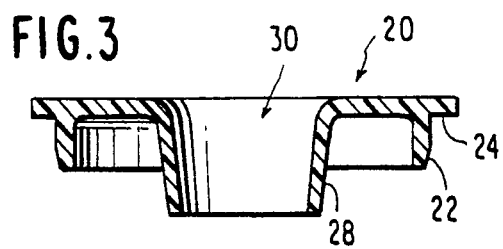
FIG. 3 is a cross-sectional side view of a cap which fits on the centrifuge vessel.
Figure 4:
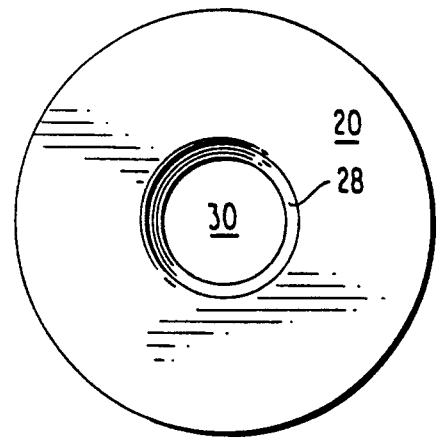
FIG. 4 is a top view of the cap of FIG. 3.
Figure 5:
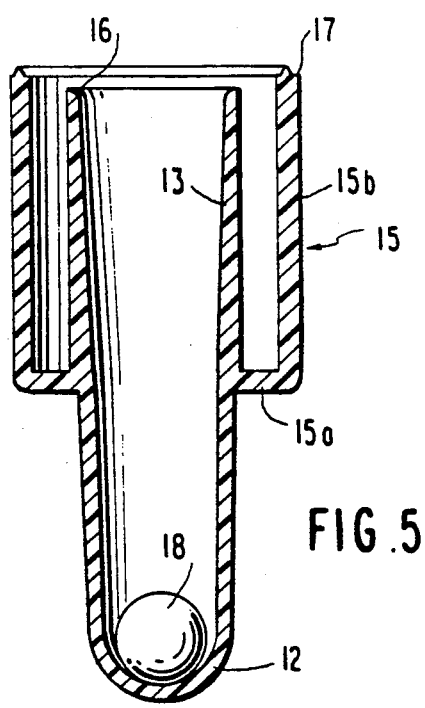
FIG. 5 is a cross-sectional side view of the centrifuge vessel showing a bead of material used for welding the cap of FIG. 3 thereto.

FIGS. 3 and 4 show that the cap 20 includes an inner flange 28, about the periphery of opening 30, that projects down into the top portion 13 of the center tube 11. The diameter of the inner flange 28 is smaller than the diameter of the top portion 13 of the center tube 11 so that fluid can pass between the flange 28 and the center tube 11, then up over the top 16 of the center tube and into the waste chamber 15. The centrifuge vessel 10 would be pre-packaged with a bound antibody coated at the base 12 of the center tube 11 or with a spherical support 18 containing bound antibody positioned in the center tube 11. If a spherical support 18 is used, it is preferred that the support 18 be placed in the tube 11 before welding the cap 20 to the top 17 of the waste chamber 15 and that the diameter of the support 18 be larger than the diameter of the inner flange 28. The inner flange 18 would help retain the solid support 18 in the center tube 11 during centrifugation and would help prevent the solid support 18 from being transported into the waste chamber 15.

In the pre-packaged configuration, a peel-off film (not shown) would cover opening 30 in the cap 20. The user would simply need to peel off the film in order to add the specimen, reagents, and wash fluid to conduct an immunoassay in the centrifuge vessel 10. The advantages of welding a cap 20 to the centrifuge vessel 10 instead of applying a film 19 over the waste chamber 15 include allowing the centrifuge vessels 10 to be individually pressure tested for leaks prior to use and avoiding the additional processing step of trimming each foil or polymer film 19 to fit neatly on the centrifuge vessel 10. Pre-pressure testing the centrifuge vessels 10 is believed to be important since the vessels 10 are subjected to intense pressure during the high speed spin.

When conducting immunoassays, a sample of fluid containing the analyte to be determined is added to the vessel's central tube 11, along with a solvent if required to reconstitute any dry reagent necessary in order to conduct the assay. If a non-competitive immunoassay is being performed, the labeled antigen or antibody is also added to the central tube 11. Addition of the sample, solvent, and other reagents can be achieved using a pipette probe or a hypodermic needle. The tube 11 contents are then be mixed by slowly rotating the vessel 10 about its longitudinal axis by means of a rotor axle whose speed may be controlled or by hand. During mixing, the analyte in the sample fluid binds to the antibody coated at the base 12 of the center tube 11 or to the antibody bound on the support 18. After an appropriate incubation period, the rotor will be rotated at a speed sufficiently great to cause any fluid within the central tube 11 to be transferred into the waste chamber 15. While the tube 11 is spinning, water or other wash solution may be intermittently introduced into the central tube 11 to wash any remaining sample and reagent out of the tube 11 and into the waste chamber 15. Once washing is completed, the bound label in the lower portion of the central tube 11 may then be quantitated by suitable means well known in the diagnostic arts.

Of course, the vessel 10 according to the present invention may be used in other procedures besides immunoassays. For example, among the many techniques used today in biochemical separations, perhaps the most efficient and selective is affinity chromatography. Affinity chromatography does not rely on general molecular properties such as size, electrical charge or density to carry out a separation. Instead, it involves a very specific interaction between two biomolecules, one of which is chemically attached (in solid phase separations) to a solid support phase, and the other of which is dissolved in solution. Such interactions are almost a universal feature of biomolecules. Specific examples would include binding between antibodies and antigens, lectins and antigens, hormones and receptors, enzymes and either substrates, coenzymes, inhibitors or activators, DNA and its complement (a repressor or catabolite gene activator for double-stranded DNA or the complement of a single strand of DNA) and messenger RNA and ribosomes. It will be readily apparent to one skilled in the separation art, that the vessel of the present invention may be modified by chemically attaching an appropriate biomolecule to either the inner surface of tube 11 or to the additional solid phase support 18, and utilizing the vessel 10 as an affinity chromatographic separation device. Once the interaction between the two biomaterials is completed, the vessel 11 may simply be spun rapidly about its longitudinal axis to remove the unbound biomaterial from the center of the tube 11 into the waste chamber 15.

While the invention has been described in terms of its preferred embodiment, which includes a center tube having a peripheral waste chamber and a bound antibody positioned in the center tube, those skilled in the art will recognize that the invention may be practiced with modification within the spirit and scope of the appended claims.

We claim:

1. A fluid transfer vessel for immunoassay designed for rotation at high speed about a central vertical axis for use in performing assays on liquid biological samples into said fluid transfer vessel, comprising:

a tube housing a bound biomaterial for binding an analyte in said liquid biological sample, said tube having a conical interior wall tapering outwardly from said central vertical axis as said wall extends from a closed bottom end of said tube to an open top end of said tube, wherein centrifugal force generated as said fluid transfer vessel rotates at high speed about said central vertical axis urges said liquid biological sample to flow along said tapered wall toward said open top end and causes said liquid biological sample to spray from said open top end outwardly away from said central vertical axis; and means, secured to said tube, for catching and holding all of said liquid biological sample sprayed from said open top end of said tube when said fluid transfer vessel is at rest with respect to rotation about said central vertical axis, said means for catching and holding said liquid biological sample preventing said liquid biological sample sprayed from said open top end of said tube from flowing back into said tube when said fluid transfer vessel is at rest.

2. A fluid transfer vessel as recited in claim 1 further comprising a cap extending over said open top end of said tube and said means for catching and holding said liquid biological sample.

3. A fluid transfer vessel as recited in claim 2 wherein said cap is a puncturable material such that said biological sample is introduced into said tube of said fluid transfer vessel through said puncturable material.

4. A fluid transfer vessel as recited in claim 3 wherein said puncturable material is foil.

5. A fluid transfer vessel as recited in claim 3 wherein said puncturable material is a plastic membrane.

6. A fluid transfer vessel as recited in claim 2 wherein said cap is a plastic material having an opening therethrough positioned above said open top end of said tube.

7. A fluid transfer vessel as recited in claim 1 wherein said means for catching and holding said biological sample sprayed from said open top end of said tube comprises a waste chamber connected to said tube having a side wall coaxial with said tube and a closed bottom end.

8. A fluid transfer vessel as recited in claim 7 wherein said waste chamber is connected to said tube on an outside wall of said tube at a point approximately half way between said closed bottom end and said open top end of said tube.

9. A fluid transfer vessel as recited in claim 7 further comprising a cap welded to said waste chamber.

10. A fluid transfer vessel for immunoassay, comprising:
    a tube having a conical interior wall tapering outwardly from a central vertical axis as said wall extends from a closed bottom end of said tube to an open top end of said tube;
    a biomaterial bound to said interior wall of said tube at or near said closed bottom end, said biomaterial being selected to bind an analyte in a liquid biological sample which can be placed in said tube; and
    a means for collecting all of said liquid biological sample when said liquid biological sample is sprayed outwardly from said open top end of said tube during high speed rotation about said central vertical axis of said tube, said means for collecting being capable of preventing said liquid biological sample transferred from said tube to said means for collecting during high speed rotation about said central vertical axis from being transferred back to said tube when said tube is at rest, said means for collecting being connected to said tube for rotation therewith.

11. A fluid transfer vessel as recited in claim 10 further comprising a means, positioned over said open top end of said tube, for directing said liquid biological sample sprayed from said open top end of said tube during high speed rotation about said central vertical axis into said means for collecting.

12. A fluid transfer vessel as recited in claim 11 wherein said means for directing comprises a cap positioned above said open top end of said tube and connected to said means for collecting.

13. A fluid transfer vessel as recited in claim 12 wherein said cap is a puncturable material.

14. A fluid transfer vessel as recited in claim 13 wherein said puncturable material is foil.

15. A fluid transfer vessel as recited in claim 13 wherein said puncturable material is a plastic membrane.

16. A fluid transfer vessel as recited in claim 12 wherein said cap is a plastic member with a bore therethrough, said plastic member being positioned such that said bore is located above said interior cylindrical wall of said tube.

17. A fluid transfer vessel as recited in claim 16 wherein said plastic member is welded to said means for collecting.

18. A fluid transfer vessel as recited in claim 10 wherein said means for collecting comprises a waste chamber connected to said tube having a side wall coaxial with said tube and a closed bottom end.

* * * * *